United States Patent
Sagawa et al.

[11] Patent Number: 6,133,238
[45] Date of Patent: Oct. 17, 2000

[54] TETRAHYDROFURANS

[75] Inventors: Hiroaki Sagawa; Shinji Okuda; Nobuko Muraki; Nobuto Koyama; Katsushige Ikai; Ikunoshin Kato, all of Otsu, Japan

[73] Assignee: Takara Shuzo Co., Ltd., Kyoto, Japan

[21] Appl. No.: 09/347,169

[22] Filed: Jul. 2, 1999

[51] Int. Cl.[7] .................. A61K 31/70; C07D 307/00; C07D 307/02

[52] U.S. Cl. ............ 514/23; 549/429; 549/483; 549/484; 536/1.1

[58] Field of Search ................ 549/484, 483, 549/429; 514/23; 536/1.1

[56] References Cited

U.S. PATENT DOCUMENTS 4,950,772  8/1990  Nohira et al. ............... 549/484

OTHER PUBLICATIONS

John S. Kiely and Suchin Huang, "The Synthesis of Methyl 1–Aryl–2–pyrrolecarboxylates," *Heterocyclic Chem.*, vol. 24, pp. 1137–1139, Jul.–Aug. 1987.

*Primary Examiner*—Howard C. Lee
*Assistant Examiner*—Everett White
*Attorney, Agent, or Firm*—Kolisch Hartwell Dickinson McCormack & Heuser

[57] ABSTRACT

2,5-dihydroxytetrahydro-2-furancarboxylic acid represented by the following formula [I], its optically active substance or salt thereof.

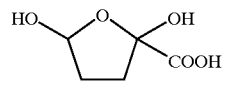

8 Claims, 5 Drawing Sheets

Incubation Time (Hours)

TETRAHYDROFURANS

TECHNICAL FIELD

The present invention relates to the novel tetrahydrofurans useful as pharmaceutical agents having a physiological activity such as anticancer action and further relates to manufacturing methods of said compound.

Prior Art

Pharmaceuticals which have been used in clinical therapy include many agents such as anticancer agents, antibiotic substances, immunopotentiators, immunomodulators, etc. (such as alkylating agents, antimetabolites and plant alkaloids) but it is hardly said that such a drug therapy has been completely established already.

Problems to be Solved by the Invention

An object of the present invention is to develop highly-safe and novel compounds having physiological actions such as an anticancer action and to offer manufacturing methods for said compounds, pharmaceutical agents containing said compounds.

Means to Solve the Problems

The present invention will be summarized to be as follows. Thus, the first feature of the present invention relates to 2,5-dihydroxytetrahydro-2-furancarboxylic acid represented by the following formula [I], its optically active substance or salt thereof.

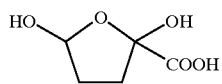

[I]

The second feature of the present invention relates to a method for the manufacture of 2,5-dihydroxytetrahydro-2-furancarboxylic acid represented by the formula [I], its optically active substance or salt thereof characterized in comprising a step where at least one compound selected from the following (a) and (b) is heat-treated.

(a) glucaric acid or glucaric acid derivative(s)

(b) a compound containing glucaric acid and/or glucaric acid derivative(s).

The third feature of the present invention relates to a pharmaceutical agent containing 2,5-dihydroxytetrahydro-2-furancarboxylic acid represented by the following formula [I], its optically active substance or salt thereof as an effective component.

In a preferred embodiment of the third feature of the present invention, said pharmaceutical agent is an anticancer agent.

PREFERRED EMBODIMENTS OF THE INVENTION

Figure 1:
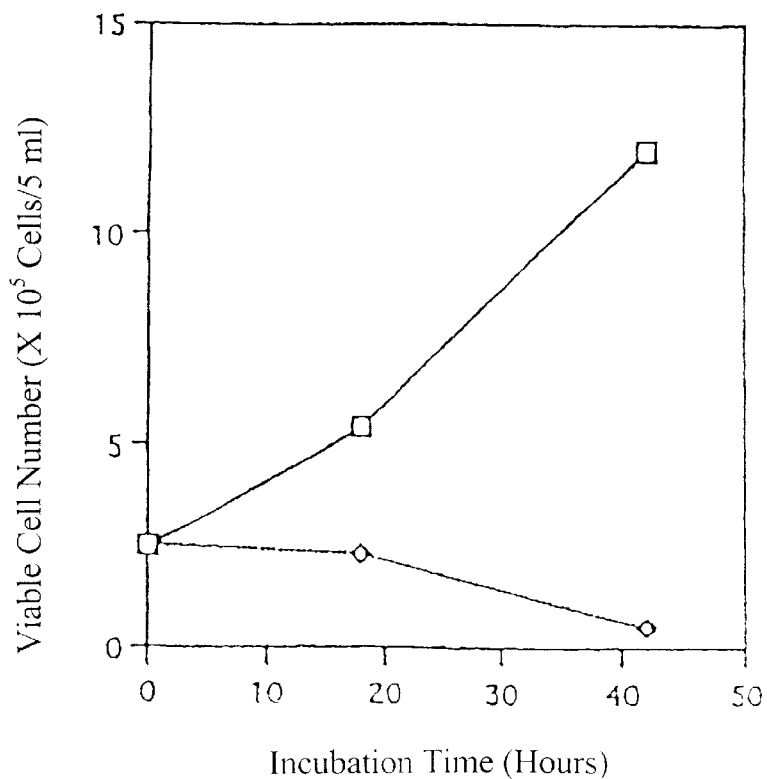
FIG. 1 shows apoptosis-inducing action of the heat-treated product of saccharic acid produced under an acidic condition.

The present invention will now be more specifically illustrated as hereinafter.

Glucaric acid is sometimes called saccharic acid having a molecular formula $C_6H_{10}O_8$ (molecular weight: 210.14) and is a dicarboxylic acid obtained by oxidation of D-glucose or oligosaccharide or polysaccharide containing the same with nitric acid or the like or obtained by oxidation of D-glucuronic acid with a bromine water as well. It can be also extracted from latex of a rubber tree (*Ficus elastica*) as a magnesium salt. Examples of glucaric acid derivatives are glucaric acid monolactone, glucaric acid dilactone, glucaric acid ester, glucaric acid amide and salts and all substances which produce 2,5-dihydroxytetrahydro-2-furancarboxylic acid represented by the formula [I] by a heating treatment are covered by the present invention. 2,5-Dihydroxytetrahydro-2-furancarboxylic acid of the present invention has asymmetric carbon atoms at 2- and 5-positions and 2,5-dihydroxytetrahydro-2-furancarboxylic acid of the present invention covers all of the four isomers, i.e. a (2S,5S) compound, a (2S,5R) compound, a (2R,5S) compound and a (2R,5R) compound. Examples of glucaric acid lactone are 1,4-monolactone, 3,6-monolactone and 1,4-3,6-dilactone and such a lactone may be used.

Examples of glucaric acid ester are methyl ester and ethyl ester and the ester can be manufactured from glucaric acid. It is also possible to manufacture an amide compound by amidation and such an amide compound may also be used in the present invention.

A compound containing glucaric acid can be obtained as an intermediate in oxidation of a polysaccharide for example. A compound attached to glucaric acid such as that containing glucaric acid lactone, glucaric acid ester and glucaric acid amide can also be prepared respectively.

In the present invention, there is no particular limitation for glucaric acid or glucaric acid derivative, a compound containing glucaric acid and/or glucaric acid derivative provided that 2,5-dihydroxytetrahydro-2-furancarboxylic acid represented by the formula [I] is produced in the heat-treated products.

As for the method of the heat treatment in the present invention, there is a method that glucaric acid or glucaric acid derivative, a compound selected from a compound containing glucaric acid and/or glucaric acid derivative is heated at room temperature to 400° C. for several seconds to several days or, preferably, at 50–200° C. for several seconds to 24 hours under neutral to acidic conditions. By this methods, heat-treated products containing 2,5-dihydroxytetrahydro-2-furancarboxylic acid can be obtained.

There is no particular limitation for the pH and concentrations of the materials upon the heat treatment so far as the concentrations are within such a range that 2,5-dihydroxytetrahydro-2-furancarboxylic acid can be produced and they may be set by taking operability, yield, etc. into consideration.

The heat treatment in the present invention may be either wet heating or dry heating although, in view of the productive efficiency of 2,5-dihydroxytetrahydro-2- furancarboxylic acid of the present invention, a wet heating is preferred. In the case of a wet heating, any of wet heating methods such as heating with steam, heating with steam under high pressure, heating under high pressure, etc. may be used while, in the case of a dry heating, any of dry heating methods such as a direct heating using dry and hot air and an indirect heating from a heat source through a partition may be used. Examples of the direct heating are a dry heating by an air stream and a dry heating by means of spraying while those of the indirect heating are a dry heating by means of a drum, etc.

In a heat-treated product, a substance showing an apoptosis-inducing action, a suppressing action for growth of cancer cells, an antibacterial action, etc. is formed and it is possible to prepare a heat-treated product containing the desired substance and having an apoptosis-inducing action, a suppressing action for growth of cancer cells, an antibacterial action, etc. by modifying the heat treatment conditions such as pH, time, temperature and material concentration depending upon the object.

2,5-dihydroxytetrahydro-2-furancarboxylic acid of the present invention, its optically active substance or salt thereof has a strong suppressing action for growth of cancer cells. 2,5-dihydroxytetrahydro-2-furancarboxylic acid or its optically active substance can be purified and isolated from a heat-treated product using this action as an index. With regard to purifying and isolating means, any of known purifying means such as chemical methods and physical methods may be used. Thus, purifying methods which have been known already such as gel filtration, fractionating using a molecular weight fractionating membrane, extraction with solvent, fractional distillation, various chromatographic methods using ion-exchange resin, etc. may be jointly used whereby 2,5-dihydroxytetrahydro-2-furancarboxylic acid or its optically active substance in a reaction product can be purified and isolated.

For example, when glucaric acid is made to react at 121° C. for 4 hours, 2,5-dihydroxytetrahydro-2-furancarboxylic acid represented by the formula [I] or its optically active substance is produced in the reaction solution and, as a result of reversed phase column chromatography of a reaction product containing this derivative, 2,5-dihydroxytetrahydro-2-furancarboxylic acid or its optically active substance can be purified and isolated.

The compound of the present invention may also be obtained by a hydration reaction of α-ketoglutarate semialdehyde. Said α-ketoglutarate semialdehyde can be obtained by a known method (*Journal of Bacteriology*, 116, 1346–1354 (1973)).

When the isolated 2,5-dihydroxytetrahydro-2-furancarboxylic acid is subjected to an optical resolution, (−)-2,5-dihydroxytetrahydro-2-furancarboxylic acid and (+)-2,5-dihydroxytetrahydro-2-furancarboxylic acid can be obtained.

Separation of the optically active substances can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used.

A method using a chiral stationary phase, a method using a chiral eluate, separation as a diastereomer, etc. may be used in an optical resolution by liquid chromatography.

A stationary phase of an amide type, that of a urea type, that of a ligand exchange type, polysaccharide-polysaccharide derivative stationary phase, protein stationary phase, polymethacrylic acid ester stationary phase, polymethacrylamide stationary phase, etc. may be used as a chiral stationary phase.

With regard to an eluting liquid, that of a hexane type, an alcohol type, an aqueous (buffer) type, etc. may be suitably used taking the combination with the above-mentioned stationary phase into consideration.

With regard to salt of 2,5-dihydroxytetrahydro-2-furancarboxylic acid of the present invention or salt of its optically active substance, salts which are acceptable as pharmaceutical agents are exemplified such as salts of alkali metals, salts of alkaline earth metals, salts with organic bases and they may be prepared by converting by means of known methods.

2,5-dihydroxytetrahydro-2-furancarboxylic acid of the present invention, its optically active substance or salt thereof has pharmacological actions such as a suppressing action for growth of cancer cells, an apoptosis-inducing action, an antibacterial action, etc. The pharmaceutical agents for therapy or prevention of, for example, cancer, infectious diseases, etc. can be manufactured by using a compound selected from 2,5-dihydroxytetrahydro-2-furancarboxylic acid of the present invention, its optically active substance or salt thereof as an effective component.

Thus, 2,5-dihydroxytetrahydro-2-furancarboxylic acid of the present invention, its optically active substance or salt thereof has a suppressing action for growth of cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colon cancer cells HCT 116, human colon cancer cells SW 480, human colon cancer cells WiDr, stomach cancer cells AGS andmyeloma cells. For example, the anticancer agent can be prepared by using a compound selected from 2,5-dihydroxytetrahydro-2-furancarboxylic acid of the present invention, its optically active substance or salt thereof as an effective component.

Agents such as anticancer agent, apoptosis-inducing agent, antibacterial agent, etc. can be manufactured, i.e. when a compound selected from 2,5-dihydroxytetrahydro-2-furancarboxylic acid of the present invention, its optically active substance or salt thereof is used as an effective component and is made into a pharmaceutical preparation by compounding with known pharmaceutical carriers. Generally, a compound selected from 2,5-dihydroxytetrahydro-2-furancarboxylic acid of the present invention, its optically active substance or salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an agent such as an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where a compound selected from 2,5-dihydroxytetrahydro-2-furancarboxylic acid, its optically active substance or salt thereof which is an effective component of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The anticancer agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated and it is not constant but, usually, the amount of a compound selected from 2,5-dihydroxytetrahydro-2-furancarboxylic acid, its optically active substance or salt thereof contained in the preparation is from 0.1 µg to 200 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

2,5-Dihydroxytetrahydro-2-furancarboxylic acid of the present invention, its optically active substance or salt thereof can be efficiently manufactured from glucaric acid. In addition to an anticancer action, 2,5-dihydroxytetrahydro-2-furancarboxylic acid in the present invention, its optically active substance or salt thereof has physiological activities such as an induction activity of the cancer cell differentiation, an apoptosis-inducing activity and an antibacterial activity and is useful as a pharmaceutical compound.

2,5-Dihydroxytetrahydro-2-furancarboxylic acid of the present invention can also be obtained by a hydrating reaction of α-ketoglutarate semialdehyde and a pharmaceutical agent which contains α-ketoglutarate semialdehyde as an effective component where said α-ketoglutarate semialdehyde is converted to 2,5-dihydroxytetrahydro-2-furancarboxylic acid upon administration is covered by the pharmaceutical agent of the present invention.

2,5-Dihydroxytetrahydro-2-furancarboxylic acid of the present invention, its optically active substance or salt thereof has a physiological action such as an anticancer action and an apoptosis-inducing action and food or beverage where 2,5-dihydroxytetrahydro-2-furancarboxylic acid of the present invention, its optically active substance or salt thereof is contained therein, added thereto and/or diluted therewith is useful as food or beverage having a physiological function such as an anticancer action and an apoptosis-inducing action.

The heat-treated product obtained by heating of at least one compound selected from glucaric acid, glucaric acid derivative and a compound containing glucaric acid and/or glucaric acid derivative shows an apoptosis-inducing action, a suppressing action for growth of cancer cells, an antibacterial action, etc. and it is possible to prepare a pharmaceutical agent such as an anticancer agent where said heat-treated product is an effective component and is combined with known pharmaceutical carriers.

Dose as an anticancer agent is appropriately decided by its form of preparation, method of administration, purpose of use and age, body weight and symptom of the patient to be treated and it is not constant but, usually, the amount of the effective component contained in the preparation is from 1 mg to 1000 mg, preferably from 10 to 200 mg, per day (for adults). Of course, the dose may vary depending upon various conditions and, therefore, the dose less than above may be sufficient in some cases while, in other cases, the dose more than above may be necessary. The agents of the present invention can be directly administered orally and, in addition, it can be added to any food and beverage so that the agents can be taken on a routine basis.

The above-mentioned heat-treated product has an antibacterial activity and may be used as an antiseptic agent for improving the preservability of food or beverage. In addition, the above-mentioned heat-treated product is added to food or beverage whereby it may be used in a method for making food or beverage antiseptic.

The form of the antibacterial agent containing the above-mentioned heat-treated product when it is added to food or beverage may be any of liquid, paste, powder, flakes, granules, etc. When an easy operation or the use by mixing with other additives are taken into consideration, it is preferred to make the agent powdery, flaky or granular by drying. With regard to the method for drying, commonly-used one such as spray drying, drum drying, shelf drying, vacuum drying, freeze drying, etc. may be used.

The antibacterial agent or antiseptic agent containing the above-mentioned heat-treated product as an effective component may be manufactured by any methods known to persons skilled in the art. In the manufacture of those agents, known additives such as fillers, stabilizers, disintegrating agents, binders, auxiliary solublizing agents, etc. may suitably be added. Further, it may be used together with ethanol, glycine, sodiumacetate, ascorbic acid, glycerol fatty acid esters, salt, EDTA and other antibacterial substances.

Amount of the above-mentioned heat-treated product to be added to food or beverage may vary depending upon the type of the food or beverage and the amount meeting with the object may be added.

One method of using the antibacterial agent containing the above-mentioned heat-treated product as an effective component is that where the agent is added to food or to beverage by an appropriate method. There is no particular limitation for a method of addition but that will do ultimately if the above-mentioned heat-treated product is contained in food or beverage by any means. Accordingly, in the use of the antibacterial agent, the term "addition" covers all methods whereby the above-mentioned heat-treated product is made to contain in food or beverage. Although the common method is to add it during the manufacturing steps of the food or beverage, a method where the food is dipped in a solution containing the above-mentioned heat-treated product may be used as well. It is also possible to conduct a method of adding it to the food together with a method of dipping the food in the solution. Examples of the food which is suitable for a dipping method are the food which does not lose its shape even in water such as fish or livestock meat paste (e.g., kamaboko [boiled fish paste] and Vienna sausage), noodles (e.g., boiled noodle) and frozen product of fish, shellfish and shrimp before freezing.

When the antibacterial agent containing the above-mentioned heat-treated product as an effective component is used as an antiseptic agent, preservability of food or beverage can be further improved. In the case of frozen food and frozen dessert, growth of contaminated microorganisms in the processing step before freezing can be suppressed whereby a very favorable result in terms of hygiene can be obtained. The antibacterial agent containing the above-mentioned heat-treated product as an effective component is effective to both gram-positive and gram-negative bacteria and is very useful, for example, to prevent infection of methicillin-resistant *Staphylococcus aureus* and prevention of infection with bacteria which cause food poisoning such as enterorrhagial *Escherichia coli* O-157.

The above-mentioned antibacterial agent shows an antibacterial activity to bacteria for dental caries and those for periodontal disease and an intraoral preparations containing the antibacterial agent of the present invention can be offered. The form of the intraoral preparation may be a known one such as liquid or paste. An example of the intraoral preparation is a dentifrice. The dentifrice may be in a known form such as liquid, paste or powder. There is no particular limitation for the amount of the above-mentioned heat-treated product in the dentifrice and, if an effective concentration to the bacteria for dental caries and for periodontal disease is contained therein, that will be enough. Known additives such as moisturizing agents, surface-active agents, binders, flavors, sweetening agents, etc. may be added to the dentifrice.

Food or beverage for apoptosis-inducing can be manufactured by making the above-mentioned heat-treated product be contained in food or beverage. Due to various physiological activities of said heat-treated product such as apoptosis-inducing activity, anticancer activity and antibacterial activity, food or beverage containing the above-mentioned heat-treated product is a healthy food or beverage for diseases accompanied by abnormal production of cells having carcinogenesis-preventing and cancer-inhibiting effects. It is also a food or beverage which is useful for maintaining the homeostasis of living body or particularly for keeping the health of stomach and utensil. In addition, due to its antibacterial activity, it is food or beverage having a very good preservation. Furthermore, the above-mentioned heat-treated product is very useful as food or beverage additives, especially antiseptic agents.

Neither 2,5-Dihydroxytetrahydro-2-furancarboxylic acid of the present invention, its optically active substance or salt thereof nor the above-mentioned heat-treated product shows toxicity to mice by oral administration.

EXAMPLES

The present invention will be further illustrated by way of the following examples although the present invention is never limited to those examples. Incidentally, "%" used in the examples stands for "% by weight".

Example 1

(1) Potassium D-saccharate (304-02; manufactured by Nacalai Tesque) was dissolved in 1N HCl to make the concentration 10 mg/ml and heated at 121° C. for 30 minutes to prepare a heat-treated product produced under an acidic condition of hydrochloric acid. Then said heat-treated produced under an acidic condition of hydrochloric acid was adjusted to pH 7.0 with NaOH, diluted to make the concentration 5 mg/ml and an apoptosis-inducing activity to human promyelocytic leukemia cells (HL-60) was measured as follows.

Thus, HL-60 (ATCC CCL-240) incubated at 37° C. in an RPMI 1640 medium (manufactured by Nissuisha) containing 10% of fetal bovine serum (manufactured by Gibco) treated at 56° C. for 30 minutes was suspended in an RPMI 1640 medium containing 10% of fetal bovine serum to make the concentration $2.5 \times 10^5$ cells/4.5 ml.

To 4.5 ml of this suspension was added 0.5 ml of the above-mentioned heat-treated product produced under an acidic condition of hydrochloric acid and incubation was carried out at 37° C. for 16 hours in the presence of 5% carbon dioxide. Further, for the sake of confirmation, the same incubation was carried out using 0.05 ml of an aqueous solution (0.1 mg/ml) of actinomycin D (manufactured by Sigma) known as a reagent for inducing the apoptosis and 0.45 ml of a physiological saline solution instead of the above heat-treated product produced under an acidic condition of hydrochloric acid.

The incubated cells were observed under an optical microscope and condensation of nuclei, contraction of cells, formation of apoptic body and a suppressing action to cell growth were confirmed in each of the incubated cells to which heat-treated product produced under an acidic condition of hydrochloric acid and actinomycin D were added. Incidentally, such a phenomenon was not noted in the controls where 0.5 ml of physiological saline solution, 0.5M aqueous solution of NaCl (the same salt concentration as the heat-treated product produced under an acidic condition of hydrochloric acid which was diluted after adjustment of pH) or non-heated potassium glucarate was added to the cells followed by incubating.

(2) When potassium saccharate was dissolved in water to make the concentration 10 mg/ml, the resulting pH was 3.95. This was heated at 121° C. for 30 minutes. The pH of the heat-treated product was 4.1. This heat-treated product produced under an acidic condition was adjusted to pH 7.0 with NaOH and its apoptosis-inducing activity and suppressing activity for growth of cells to HL-60 cells were measured by a method of Example 1-(1) whereupon this sample had both activities.

The results are shown in FIG. 1. Thus FIG. 1 shows the relation between the incubation time and viable cell number in the culture when the heat-treated product of saccharic acid produced under an acidic condition was added to the culture of HL-60 cells to make the concentration 1 mg/ml wherein the abscissa indicates an incubation time (hours) while the ordinate indicates a viable cell number ($\times 10^5$ cells/5 ml) in the culture. In FIG. 1, an open square is a fraction to which no sample was added (control) and an open rhomb is a fraction to which the heat-treated product of saccharic acid produced under an acidic condition was added.

(3) D-saccharic acid 1,4-lactone monohydrate (304-35; manufactured by Nacalai Tesque) was dissolved in 1N HCl to make the concentration 10 mg/ml and heated at 121° C. for 30 minutes to prepare a heat-treated product produced under an acidic condition of hydrochloric acid. Then said heat-treated product produced under an acidic condition of hydrochloric acid was adjusted to pH 7.0 with NaOH, diluted to make the concentration 5 mg/ml and an apoptosis-inducing activity and a suppressing activity for growth of cells to HL-60 cells were measured by a method of Example 1-(1) whereupon this sample had both activities. Incidentally, non-heated D-saccharic acid 1,4-lactone had no activity.

(4) D-saccharic acid 1,4-lactone monchydrate was dissolved in water to make the concentration 10 mg/ml, adjusted to pH 7.0 with NaOH and heated at 121° C. for 30 minutes. The pH of the heat-treated product was 4.3. This heat-treated product was adjusted to pH 7.0 with NaOH and an apoptosis-inducing activity and a suppressing activity for growth of cells to HL-60 cells were measured by the method of Example 1-(1) whereupon this sample had both activities. Incidentally, non-heated D-saccharic acid 1,4-lactone had no activity.

Figure 2:
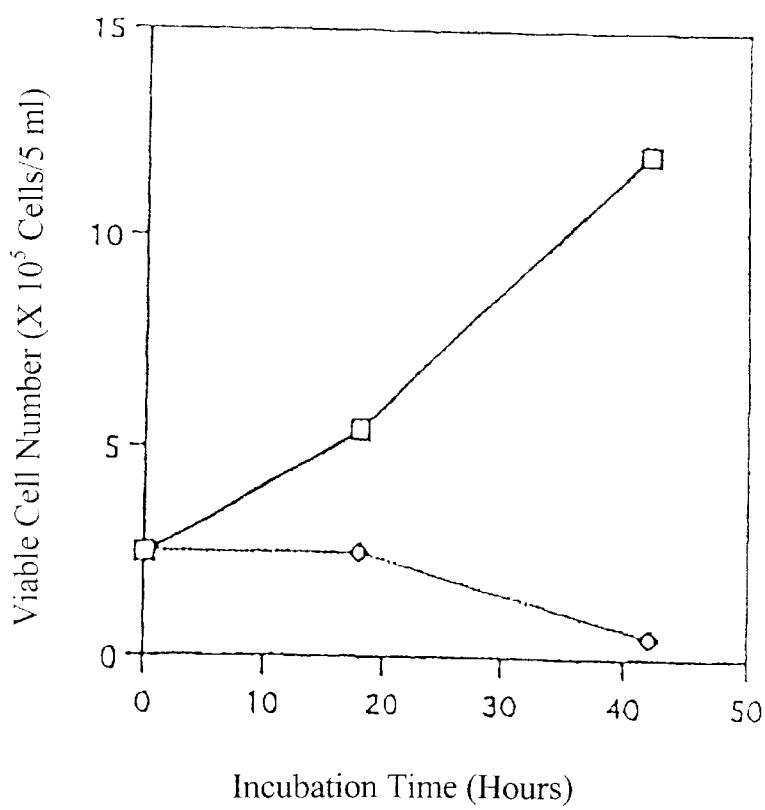
FIG. 2 shows apoptosis-inducing action of the heat-treated product of D-saccharic acid 1,4-lactone.

The results are shown in FIG. 2. Thus FIG. 2 shows the relation between the incubation time and viable cell number in the culture when the heat-treated product of D-saccharic acid 1,4-lactone was added to the culture of HL-60 cells to make the concentration 1 mg/ml wherein the abscissa indicates an incubation time (hours) while the ordinate indicates a viable cell number ($\times 10^5$ cells/5 ml) in the culture. In FIG. 2, an open square is a fraction to which no sample was added (control) and an open rhomb is a fraction to which the heat-treated product of D-saccharic acid 1,4-lactone was added.

(5) Potassium D-saccharate was dissolved in water to make the concentration 10 mg/ml whereupon the pH was 3.95. This was heated at 121° C. for 30 minutes, 1 hour, 2 hours, 4 hours and 16 hours. Each of the heated and non-heated products was adjusted to around pH 7 and sterilized using a filter of 0.22 μm to prepare a sample for measuring an apoptosis-inducing activity and a suppressing activity for growth of cells. The sample was diluted to an extent of 2-, 5-, 10-, 20-, 50- and 100-fold, its suppressing activity for growth of cells was measured using HL-60 cells (human promyelocytic leukemia cells) and potency of the activity was compared.

Thus, 10 μl of each of the diluted solutions or 10 μl of water were placed in a 96-well microtiter plate. An RPMI 1640 medium (100 μl) containing 10% fetal bovine serum and 5000 HL-60 cells was added thereto and incubation was carried out at 37° C. for 48 hours in the presence of 5% carbon dioxide gas. A saline solution (10 μl) buffered with a phosphate containing 5 mg/ml of 3-(4,5-dimethylthiazol-2-yl)-2,5-diphenyltetrazolium bromide (MTT; manufactured by Sigma) was added thereto, the mixture was incubated for 4 hours more and the state of growth of the cells was observed under a microscope. Further, 100 μl of 2-propanol containing 0.04N HCl were added, the mixture was stirred well, an absorbance at 590 nm was measured and it was defined as a degree of the cell growth (an MTT method).

The result was that the non-heated potassium D-saccharate solution had no suppressing activity for growth of cells while the potassium D-saccharate solutions heated for 30 minutes, 1 hour, 2 hours, 4 hours and 16 hours were confirmed to show a suppressing activity for growth of cells to an extent of 2-, 2-, 5-, 10- and 20-fold dilutions, respectively. In addition, condensation of nuclei, contraction of cells and formation of apoptic body were confirmed in the incubated cells at the sample concentrations where the suppressing activity for growth of cells was noted whereby the apoptosis-inducing activity was ascertained.

In the meanwhile, a part of each of the heat-treated products was sampled and concentrated to dryness and 1/20 by volume of the resulting sample was dissolved in 50% methanol. The concentrate solution was spotted on two sheets of thin layer silica gel (Silica Gel 60 F254; manufactured by Merck) and developed with a developer (n-butyl acetate:acetic acid:distilled water=3:1:1). One of the thin layers after the development was irradiated with ultraviolet ray of short waves to detect the spots. This was further sprayed with an $AgNO_3$—$NH_3$ solution (a mixture of 0.1N aqueous solution of $AgNO_3$ and a 5N $NH_3$ in the same volume) followed by heating to detect the spots. Another thin layer was sprayed with a mixture of ethanol and sulfuric acid (ethanol:sulfuric acid=1:1) followed by heating to detect the spots.

As a result of the thin layer silica gel chromatography, the spots which increased with a lapse of time were confirmed to be present at the Rf values of about 0.13, about 0.06 and about 0.03 and such an increasing tendency was in a parallel relationship with the increase in the suppressing activity for growth of cells which was assayed by an MTT method.

(6) D-saccharic acid 1,4-lactone monohydrate (manufactured by Nacalai Tesque) was dissolved in water to make the concentration 10 mg/ml whereupon the pH was 2.5. This was heated at 121° C. for 30 minutes, 1 hour, 2 hours, 4 hours and 16 hours. Each of the heat treated products and non-heated one was adjusted to pH of about 7 and sterilized using a filter of 0.22 μm to prepare a sample for measuring the suppressing activity for growth of cells. Those samples for measuring the suppressing activity for growth of cells were diluted to an extent of 2-, 5-, 10-, 20-, 50- and 100-fold, their suppressing activity for growth of cells to HL-60 cells was measured by an MTT method mentioned in Example 1-(5) and the potency of the activity was compared. In addition, condensation of nuclei of the incubated cells, contraction of cells and formation of apoptic body were observed and potency of the apoptosis-inducing activity was compared thereby.

The result was that the non-heated D-saccharic acid 1,4-lactone solution had neither cell growth suppression activity nor apoptosis-inducing activity while the heat-treated products of D-saccharic acid 1,4-lactone heated for 30 minutes, 1 hour, 2 hours, 4 hours and 16 hours were confirmed to have suppressing activity for growth of cells and apoptosis-inducing activity to an extent of 1-, 2-, 5-, 10- and 50-dilutions, respectively.

In the meanwhile, a part of the each of the heat-treated products was sampled and concentrated to dryness followed by dissolving in 1/20 by volume of 50% methanol. This was subjected to a thin layer silica gel chromatography by the method mentioned in Example 1-(5).

As a result of the thin layer silica gel chromatography, the spots which increased with a lapse of time were confirmed to be present at the Rf values of about 0.13, about 0.06 and about 0.03 and such an increasing tendency was in a parallel relationship to the increase in the suppressing activity for growth of cells assayed by an MTT method.

Then, 1.5 ml of heat-treated product of D-saccharic acid 1,4-lactone were concentrated to dryness, the resulting product was re-dissolved in 60 μl of 50% methanol and 50 μl thereof were developed by a thin layer silica gel chromatography by the same manner as in Example 1-(5). Then silica gels at the points where Rf values were about 0.13, between 0.13–0.16, about 0.06 and about 0.03 and also at the starting point of this thin layer silica gel were scratched off and each of them was extracted with 500 μl of 50% methanol. The extract was concentrated to dryness, the resulting product was dissolved in 100 μl of sterilized distilled water, then the suppressing activity for growth of cells and the apoptosis-inducing activity were measured by the same manner as in Example 1-(5) and activity was found at the area from the starting point to the point where Rf value was 0.13.

(7) D-saccharic acid 1,4-lactone monohydrate (manufactured by Nacalai Tesque) was dissolved in water to make the concentration 10 mg/ml whereupon the pH was 2.5. This was heated at 121° C. for 4 hours and 16 hours.

Those heated products of D-saccharic acid 1,4-lactone and non-heated one were subjected to a mass analysis in a negative ion mode using an API-III (manufactured by Sciex). As a result, it was found that, in the heated product, substances having molecular weights of 130, 148, etc. increased corresponding to an increase in the heating time and the apoptosis-inducing activity.

Example 2

(1) A sample (100 ml) obtained by heating 1% D-saccharic acid 1,4-lactone monohydrate at 121° C. for 4 hours was freeze-dried and re-dissolved in 2 ml of water. A part of this re-dissolved solution was filtered through a Cosmonice filter (440-84; manufactured by Nacalai Tesque) of 0.5 μm, subjected to an HPLC using TSK gel ODS-80Ts (6 mm×250 mm; manufactured by Tosoh) at a flow rate of 0.5 ml/minute using a 0.1% aqueous solution of trifluoroacetic acid (349-01; manufactured by Nacalai Tesque) as a mobile phase and a detection was conducted at the absorbance of 210 nm whereupon ten main peaks were confirmed. Then, each of the peaks was collected by the same method and sterilized using a filter of 0.22 μm to prepare a sample for checking the suppressing activity for growth of cancer cells. The samples were diluted to an extent of 1-, 2-, 4-, 8-, 16- and 32-fold, then an apoptosis-inducing activity and a suppressing activity for growth of cells to human promyelocytic leukemia cells (HL-60 cells) were measured by the method mentioned in Example 1-(5) and potency of the activity was compared.

As a result, the activity was confirmed at the peak where the retention time was 5.6 minutes and the suppressing activity for growth of cancer cells and apoptosis-inducing activity were confirmed up to a 32-fold diluted product of the peak of retention time of 5.6 minutes.

(2) The peak of the retention time of 5.6 minutes mentioned in Example 2-(1) was collected and concentrated to dryness in vacuo. Mass analysis of this sample was conducted using a DX302 mass spectrometer (manufactured by Nippon Denshi). Further, this was dissolved in heavy water and its structure was analyzed by means of a nuclear magnetic resonance (NMR). As to the nuclear magnetic resonance spectrometer, JNM-A500 (manufactured by Nippon Denshi) was used. Then, this was dissolved in water to make the concentration 88 μg/ml and its ultraviolet absorption spectrum was measured using a UV-2500 spectrophotometer (manufactured by Shimadzu). The result is mentioned below.

Characteristics of the samples are given in the attached FIG. 3 to FIG. 6. Thus, all of FIGS. 3–6 are the drawings which show the characteristics of 2,5-dihydroxytetrahydro-2-furancarboxylic acid of the present invention.

Figure 3:
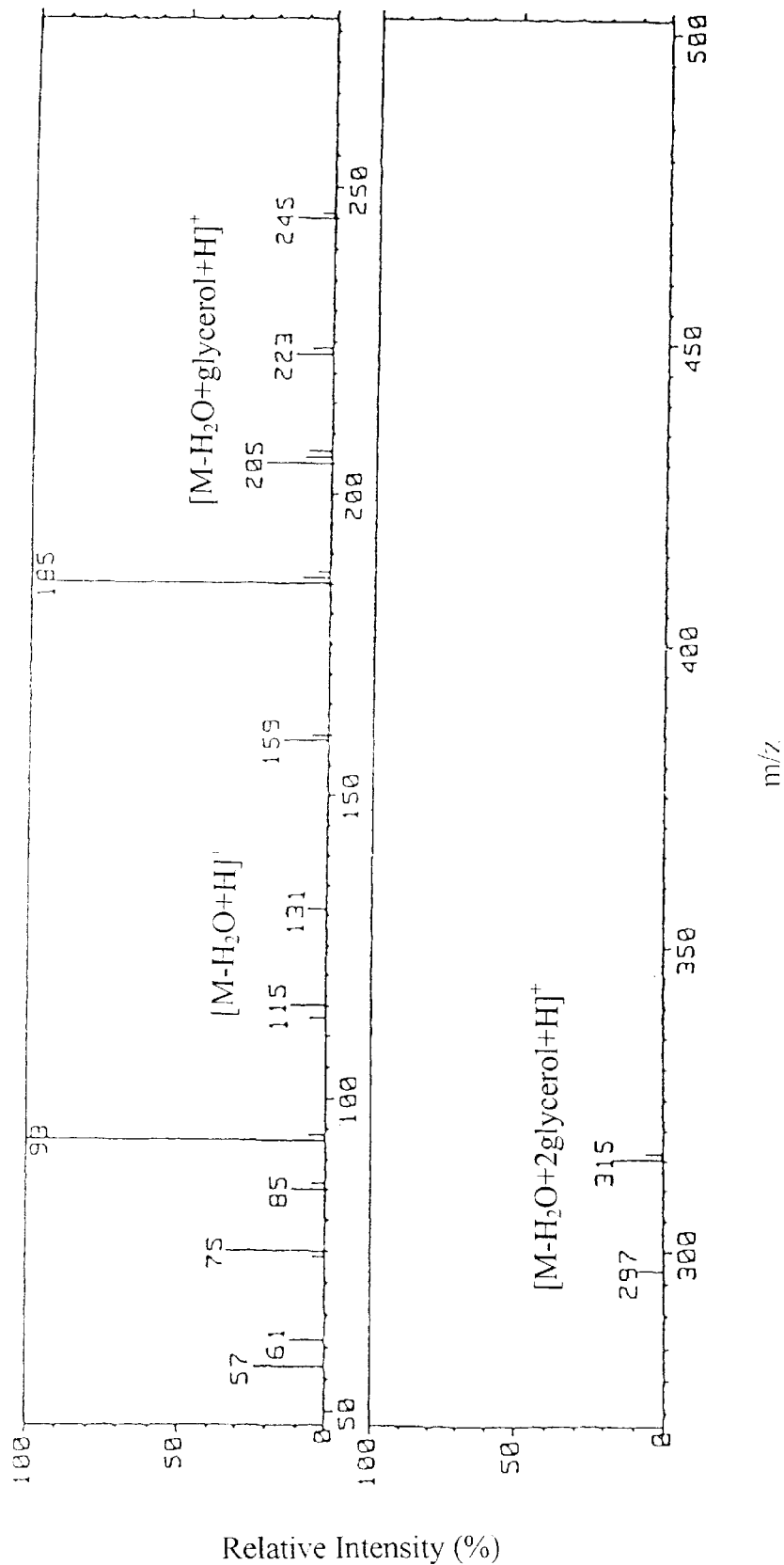
FIG. 3 shows a mass spectrum of 2,5-dihydroxytetrahydro-2-furancarboxylic acid.
Figure 4:
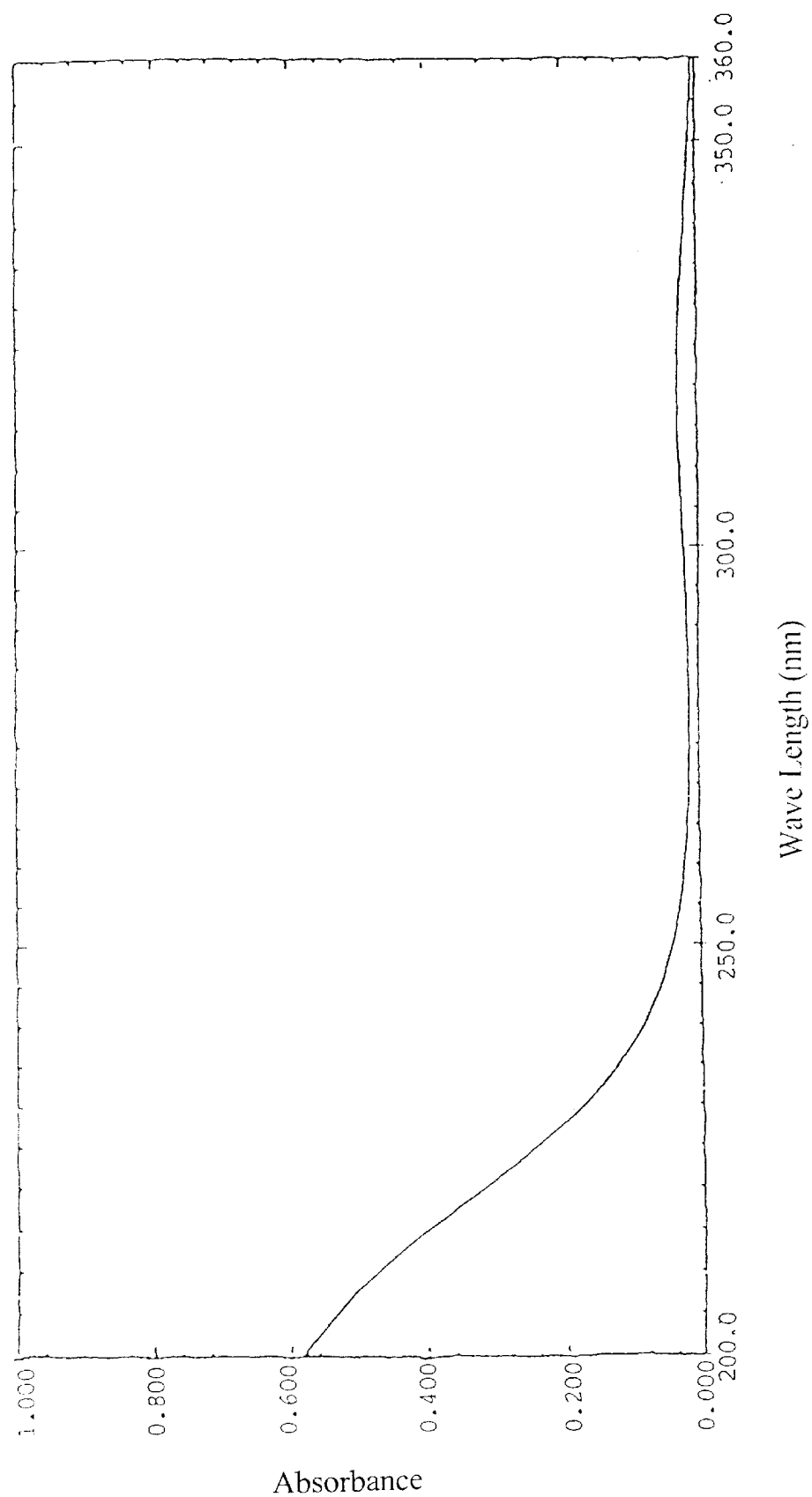
FIG. 4 shows an ultraviolet absorption spectrum of 2,5-dihydroxytetrahydro-2-furancarboxylic acid.
Figure 5:
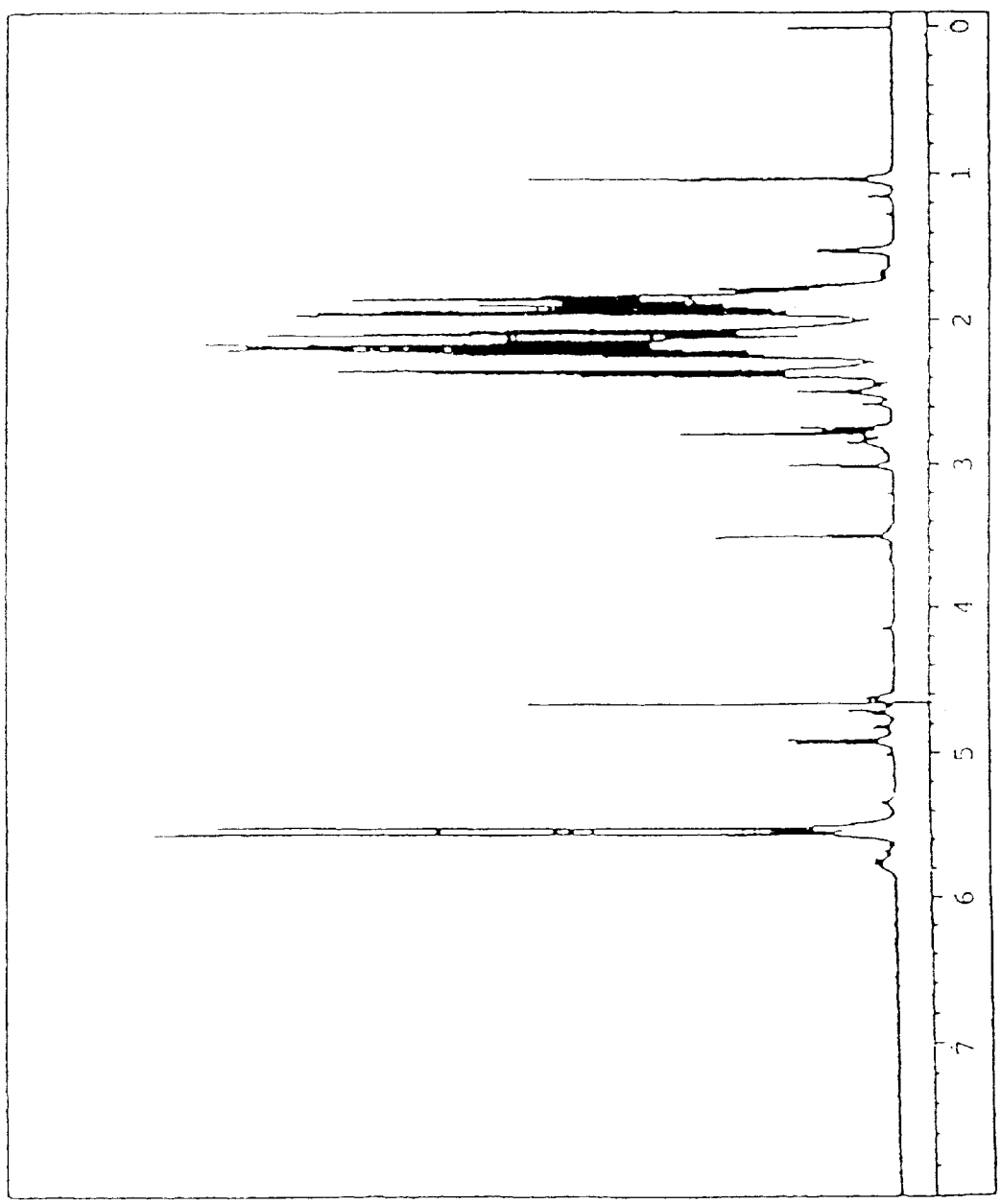
FIG. 5 shows a $^1$H-NMR spectrum of 2,5-dihydroxytetrahydro-2-furancarboxylic acid.
Figure 6:
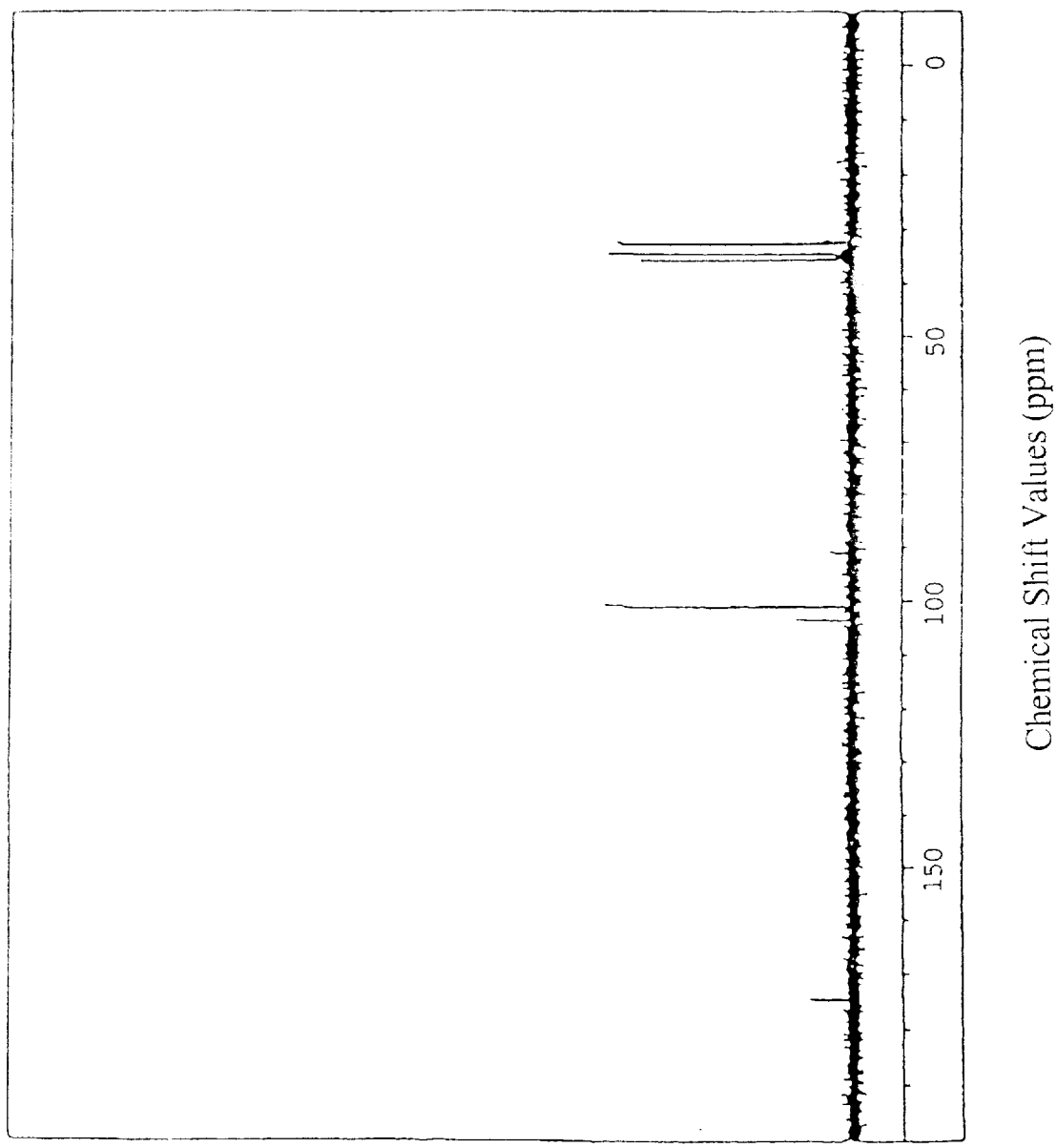
FIG. 6 shows a $^{13}$C-NMR pectrum of 2,5-dihydroxytetrahydro-2-furancarboxylic acid.

FIG. 3 shows a mass spectrum [ordinate indicates a relative intensity (%) while abscissa indicates m/z], FIG. 4 shows an ultraviolet absorption spectrum [ordinate indicates absorbance while abscissa indicates wave length (nm)], FIG. 5 shows a $^1$H-NMR spectrum [ordinate indicates signal intensity while abscissa indicates chemical shift values (ppm)] and FIG. 6 shows a $^{13}$C-NMR spectrum [ordinate indicates signal intensity while abscissa indicates chemical shift values (ppm)].

FAB-MS: m/z 131 [M–H$_2$O+H]$^+$

UV: $\lambda_{max}$ terminal absorption

Diastereomer 1

$^1$H-NMR: δ 1.83 (1H, m, 4-H), 1.94 (1H, m, 3-H), 2.18 (1H, m, 4-H), 2.36 (1H, m, 3-H), 5.55 (1H, d—d, J=2.0, 5.0 Hz, 5-H).

$^{13}$C-NMR: δ 32.1, 34.3, 100.5, 103.3, 174.4.

Diastereomer 2

$^1$H-NMR: δ 1.88 (1H, m, 4-H), 2.07 (1H, m, 3-H), 2.15 (1H, m, 4-H), 2.23 (1H, m, 3-H), 5.51 (1H, d—d, J=3.5, 5.0 Hz, 5-H).

$^{13}$C-NMR: δ 32.7, 35.5, 101.1, 103.5, 174.7.

Incidentally, chemical shift value of HOD was made 4.65 ppm in $^1$H-NMR while that of dioxane was made 67.4 ppm in $^{13}$C-NMR.

From those values, it was clarified that the present sample was a mixture of (2S, 5S)-2,5-dihydroxytetrahydro-2-furancarboxylic acid represented by the following formula [II] and an antipode thereof and (2S, 5R)-2,5-dihydroxytetrahydro-2-furancarboxylic acid represented by the following formula [III] and an antipode thereof. Incidentally, one of the diastereomer 1 and the diastereomer 2 is a substance represented by the formula [II], an antipode thereof or a mixture thereof while another is a substance represented by the formula [III], an antipode thereof or a mixture thereof.

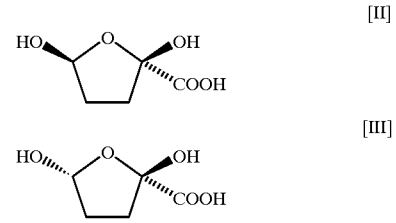

Example 3

α-Ketoglutarate semialdehyde was prepared by a method mentioned in *Journal of Bacteriology*, 116, 1346–1354 (1973) and then subjected to a hydration reaction to give 2,5-dihydroxytetrahydro-2-furancarboxylic acid.

Example 4

(1) Potassium D-saccharate was dissolved in distilled water to make the concentration 1% and heated at 120° C. for 4 hours. An antibacterial activity was tested using the resulting heat-treated potassium saccharate.

*Escherichia coli* HB 101 was subjected to a seed culture in an L-broth (containing 1% of tryptone, 0.5% of yeast extract and 0.5% of NaCl; pH 7.0) overnight. The seed culture liquid (5 μl) was heated to a medium prepared by adding 50 μl or 500 μl of heat-treated potassium saccharate to 5 ml of the L-broth and also to a medium where nothing was added to the L-broth and subjected to a shake culture to measure the growth. Measurement was conducted at the initiation of the incubation and also at 6.5 hours thereafter using a Fuji Digital Turbidimeter (sold by Fuji Kogyo KK; manufactured by Akimoto Denki Seisakusho) under the condition where the adjusted scale was 82.3 and value obtained by subtracting the value at the initiation from that after 6.5 hours was defined as a growth. As a result, an antibacterial activity was noted in the heat-treated potassium saccharate as shown in Table 1.

TABLE 1

| Amount Added ($\mu$ 1/5 ml) | Growth (Turbidity) |
|---|---|
| 0 | 167 |
| 50 | 159 |
| 500 | 120 |

(2) D-saccharic acid 1,4-lactone monohydrate was dissolved in distilled water to make the concentration 1% and heated at 120° C. for 4 hours. Antibacterial activity was tested using this heat-treated D-saccharic acid 1,4-lactone by the method mentioned in Example 4-(1). As a result, an antibacterial activity was noted in the heat-treated D-saccharic acid 1,4-lactone as shown in Table 2.

TABLE 2

| Amount Added ($\mu$ 1/5 ml) | Growth (Turbidity) |
|---|---|
| 0 | 167 |
| 50 | 154 |
| 500 | 15 |

Example 5

Injection Preparation (1) A 0.1% aqueous solution of 2,5-dihydroxytetrahydro-2-furancarboxylic acid dissolved in distilled water was prepared and was subjected to an aseptic filtration to give an injection preparation.

(2) Concentrated and dried product after neutralization of the heat-treated D-saccharic acid as mentioned in Example 1-(2) was dissolved in distilled water for injection to prepare a 1% solution. This solution was filled in a vial for freeze-drying in an amount of 10 mg calculated as a dry substance of the supernatant fraction and subjected to a freeze-drying. A physiological saline solution (2 ml) was attached thereto as a liquid for dissolution.

Similarly was prepared an injection preparation using a heat-treated product of D-saccharic acid 1,4-lactone mentioned in Example 1-(4).

Example 6

Tablets

Tablets were prepared in accordance with the following formulation.

| Heat-treated potassium D-saccharate | 10 mg |
| Corn starch | 65 mg |
| Carboxymethyl cellulose | 20 mg |
| Polyvinylpyrrolidone | 3 mg |
| Magnesium stearate | 2 mg |
| Each tablet consisting of | 100 mg in total |

The freeze-dried product of neutralized product of heat-treated D-saccharic acid mentioned in Example 1-(2) was used.

Merit of the Invention

In accordance with the present invention, 2,5-dihydroxytetrahydro-2-furancarboxylic acid or its optical isomer or a salt thereof having physiological actions such as an anticancer action, a cancer cell growth suppressing action, an apoptosis-inducing action and an antibacterial action and having a high safety is offered and, further, a pharmaceutical agent (particularly, an anticancer agent) containing said compound having a physiological activity function is offered.

What is claimed is:

1. 2,5-dihydroxytetrahydro-2-furancarboxylic acid represented by the following formula [I], its optically active substance or salt thereof.

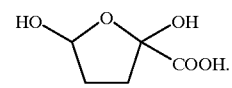

[I]

2. A process for producing 2,5-dihydroxytetrahydro-2-furancarboxylic acid represented by the following formula [I], its optically active substance or salt thereof, comprising a step where at least one compound selected from the following (a) and (b) is heat-treated:
   (a) glucaric acid or glucaric acid derivative(s)
   (b) a compound attached to glucaric acid and/or glucaric acid derivative(s).

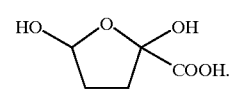

[I]

3. A pharmaceutical composition comprising:
   2,5-dihydroxytetrahydro-2-furancarboxylic acid represented by the following formula [I], its optically active substance or salt thereof as an active ingredient; and
   a pharmaceutical carrier.

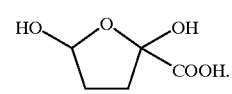

[I]

4. A pharmaceutical composition according to claim 3, wherein said pharmaceutical composition is an anticancer agent.

5. A pharmaceutical composition according to claim 3, wherein said pharmaceutical carrier is selected from the group comprising starch, lactose, sugar, mannitol, carboxymethyl cellulose, corn starch, and inorganic salts.

6. A pharmaceutical composition according to claim 5, further comprising an additive selected from the group comprising binders, disintegrating agents, surface-active agents, lubricants, fluidity promoters, taste-correctiveness, coloring agents, and flavors.

7. A pharmaceutical composition according to claim 3, wherein said pharmaceutical carrier is a diluent selected from the group comprising distilled water, physiological saline solution, aqueous solution of glucose, vegetable oil for injection, sesame oil, peanut oil, soybean oil, corn oil, propylene glycol, and polyethylene glycol.

8. A pharmaceutical composition according to claim 7, further comprising an additive selected from the group comprising bactericides, stabilizers, isotonic agents, and analgesics.

* * * * *

UNITED STATES PATENT AND TRADEMARK OFFICE
CERTIFICATE OF CORRECTION

PATENT NO : 6,133,238
DATED : October 17, 2000
INVENTOR(S): Hiroaki Sagawa et al.

It is certified that error appears in the above-identified patent and that said Letters Patent is hereby corrected as shown below:

<u>ON THE TITLE PAGE</u>

[22] PCT Filed: January 19, 1998

[86] PCT No.: PCT/JP98/00190

§ 371 Date: July 2, 1999

§ 102(e) Date: July 2, 1999

[87] PCT Pub. No.: WO98/32749

PCT Pub. Date: July 30, 1998

[30] Foreign Application Priority Data

Jan. 21, 1997 [JP] Japan ........ 25755/97
May 21, 1997 [JP] Japan ....... 146067/97

Signed and Sealed this

Eighth Day of May, 2001

Attest:

NICHOLAS P. GODICI

Attesting Officer

Acting Director of the United States Patent and Trademark Office